(12) United States Patent
Yang et al.

(10) Patent No.: US 12,626,801 B2
(45) Date of Patent: May 12, 2026

(54) DETERMINING A REGIMEN TO IMPROVE HEALTH PARAMETER OF AN OBJECT

(71) Applicant: International Business Machines Corporation, Armonk, NY (US)

(72) Inventors: Xiao Ling Yang, Xi'an (CN); Lei Tian, Xi'an (CN); Jing James Xu, Xi'an (CN); Si Er Han, Xi'an (CN); Xue Ying Zhang, Xi'an (CN); Xiao Ming Ma, Xi'an (CN)

(73) Assignee: International Business Machines Corporation, Armonk, NY (US)

( * ) Notice: Subject to any disclaimer, the term of this patent is extended or adjusted under 35 U.S.C. 154(b) by 56 days.

(21) Appl. No.: 18/423,415

(22) Filed: Jan. 26, 2024

(65) Prior Publication Data

US 2025/0246286 A1 Jul. 31, 2025

(51) Int. Cl.
| | |
|---|---|
| *G06F 8/70* | (2018.01) |
| *G06F 8/65* | (2018.01) |
| *G16H 20/30* | (2018.01) |
| *G16H 50/20* | (2018.01) |

(52) U.S. Cl.
CPC .............. *G16H 20/30* (2018.01); *G06F 8/65* (2013.01); *G06F 8/70* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 10,453,008 B2 | 10/2019 | Chu et al. | |
| 11,602,279 B2 | 3/2023 | Ahmed et al. | |

| | | | | |
|---|---|---|---|---|
| 2001/0012913 A1* | 8/2001 | Iliff | | G16H 50/20 |
| | | | | 128/920 |
| 2003/0229513 A1* | 12/2003 | Spertus | | G06Q 10/10 |
| | | | | 705/2 |
| 2005/0203773 A1* | 9/2005 | Soto | | G16H 50/70 |
| | | | | 705/2 |

(Continued)

FOREIGN PATENT DOCUMENTS

| | | |
|---|---|---|
| CN | 109011518 B | 5/2020 |

OTHER PUBLICATIONS

"A Thorough Introduction to Holt-Winters Forecasting"; Lleyton Ariton; Analytics Vidhya; Feb. 22, 2021 (Year: 2021).*

*Primary Examiner* — John A Pauls

(74) *Attorney, Agent, or Firm* — CANTOR COLBURN LLP; Kelsey Skodje

(57) ABSTRACT

A process includes receiving a set of static characteristics, a set of dynamic characteristics, and a health objective of a target object. A set of reference object data is retrieved and includes multiple reference objects of the same type as the target object. The reference object data includes the same data as the target object data. The dynamic data of the target object and the reference objects is parameterized over time. Each a set of dynamic characteristics for each reference object is split into a plurality of reference profiles. A set of similar reference profiles having a higher similarity metric than a remainder of the reference profiles is identified. A goal difference between the health objective of the target object and an end state of the similar reference profiles is determined. The reference profile having the smallest goal difference is identified and a corresponding health regimen is implemented.

12 Claims, 6 Drawing Sheets

(56)          References Cited

U.S. PATENT DOCUMENTS

| | | | |
|---|---|---|---|
| 2016/0354039 A1* | 12/2016 | Soto ......................... | A61B 5/74 |
| 2020/0152330 A1 | 5/2020 | Anushiravani et al. | |
| 2020/0233774 A1 | 7/2020 | Toledano | |
| 2021/0174919 A1 | 6/2021 | Vaughan | |

* cited by examiner

TIME t

| User | Age | HEIGHT | CBC | RLF | HR | BP |
|------|-----|--------|-----|-----|-----|-----|
| A | 23 | 180 CM | 100 | Bad | 80 | High |
| B | 35 | 163 CM | 150 | Normal | 100 | Low |
| C | 47 | 176 CM | 120 | Good | 120 | Normal |
| D | 59 | 158 CM | 170 | Normal | 150 | High |

1

DETERMINING A REGIMEN TO IMPROVE HEALTH PARAMETER OF AN OBJECT

BACKGROUND

The present invention generally relates to monitoring and tracking an object's health, and more specifically, to a process for determining a regimen to optimize a health parameter of the object.

Tracking the health of an object typically involves monitoring one or more specific health parameters over time. Objects that are tracked in this way can include individual adult people with a health parameter focused on a fitness or sports goal, computer servers or systems within a cloud environment with a health parameter focused on a lifecycle goal, manufacturing systems with a health parameter directed toward minimization of downtime, or any similar systems. Consequently, attempts to improve the overall health of the object often focus on activities that are specifically targeted to improving the monitored parameters instead of toward providing a general health benefit.

SUMMARY

Embodiments of the present invention are directed to a computer-implemented method for monitoring the health of an object. A non-limiting example of the computer-implemented method includes receiving a set of static characteristics, a set of dynamic characteristics, and a health objective of a target object. A set of reference object data is retrieved and includes multiple reference objects of the same type as the target object. The reference object data includes the same data as the target object data. The dynamic data of the target object and the reference objects is parameterized over time. Each a set of dynamic characteristics for each reference object is split into a plurality of reference profiles. A set of similar reference profiles having a higher similarity metric than a remainder of the reference profiles is identified. A goal difference between the health objective of the target object and an end state of the similar reference profiles is determined. The reference profile having the smallest goal difference is identified and a corresponding health regimen is implemented. Embodiments of the present invention likewise include a system and a computer program product for implementing the same.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

2

Figure 1:
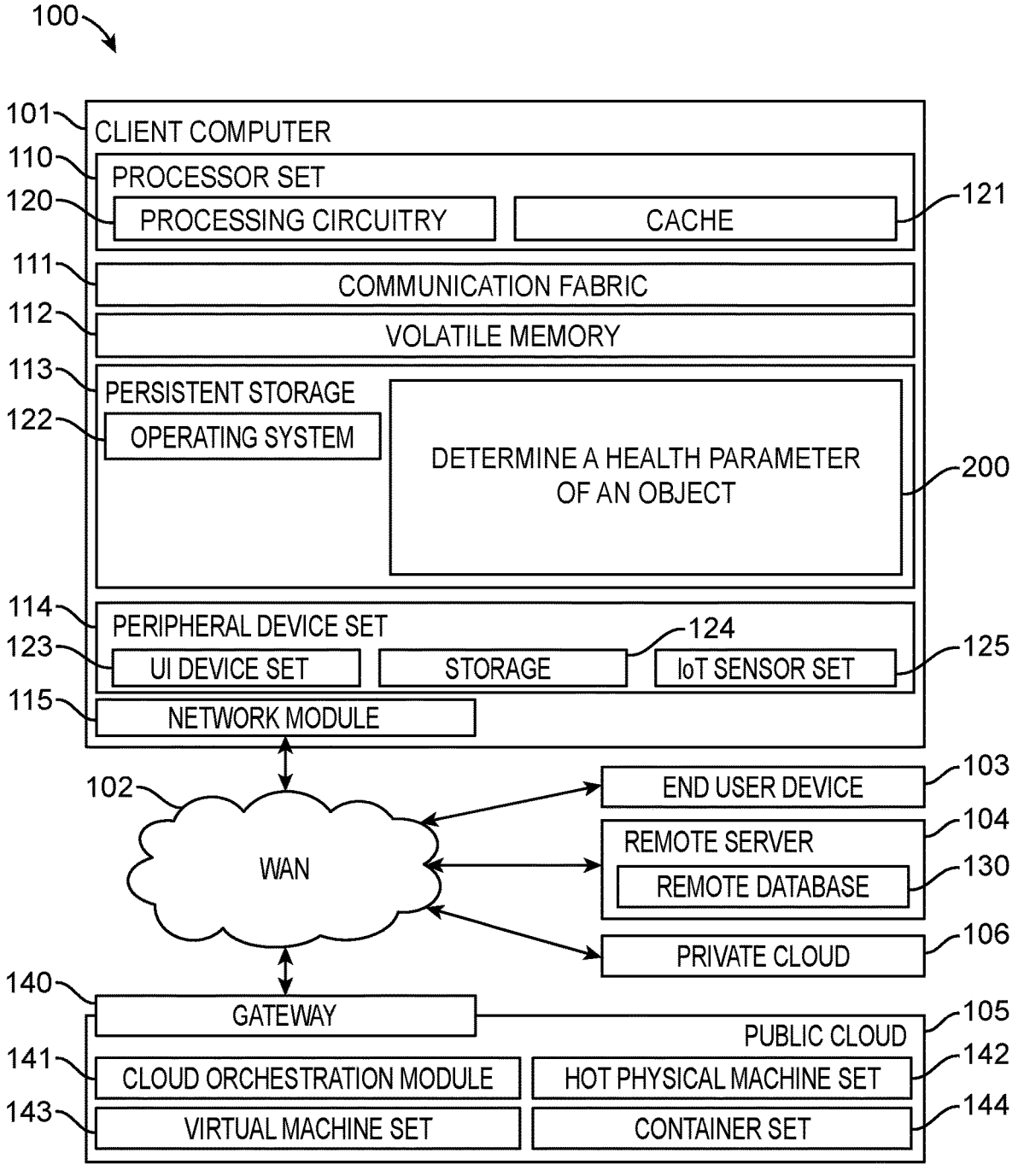
FIG. 1 depicts one exemplary cloud computing system configured to implement the system and method according to one embodiment.
Figure 3:
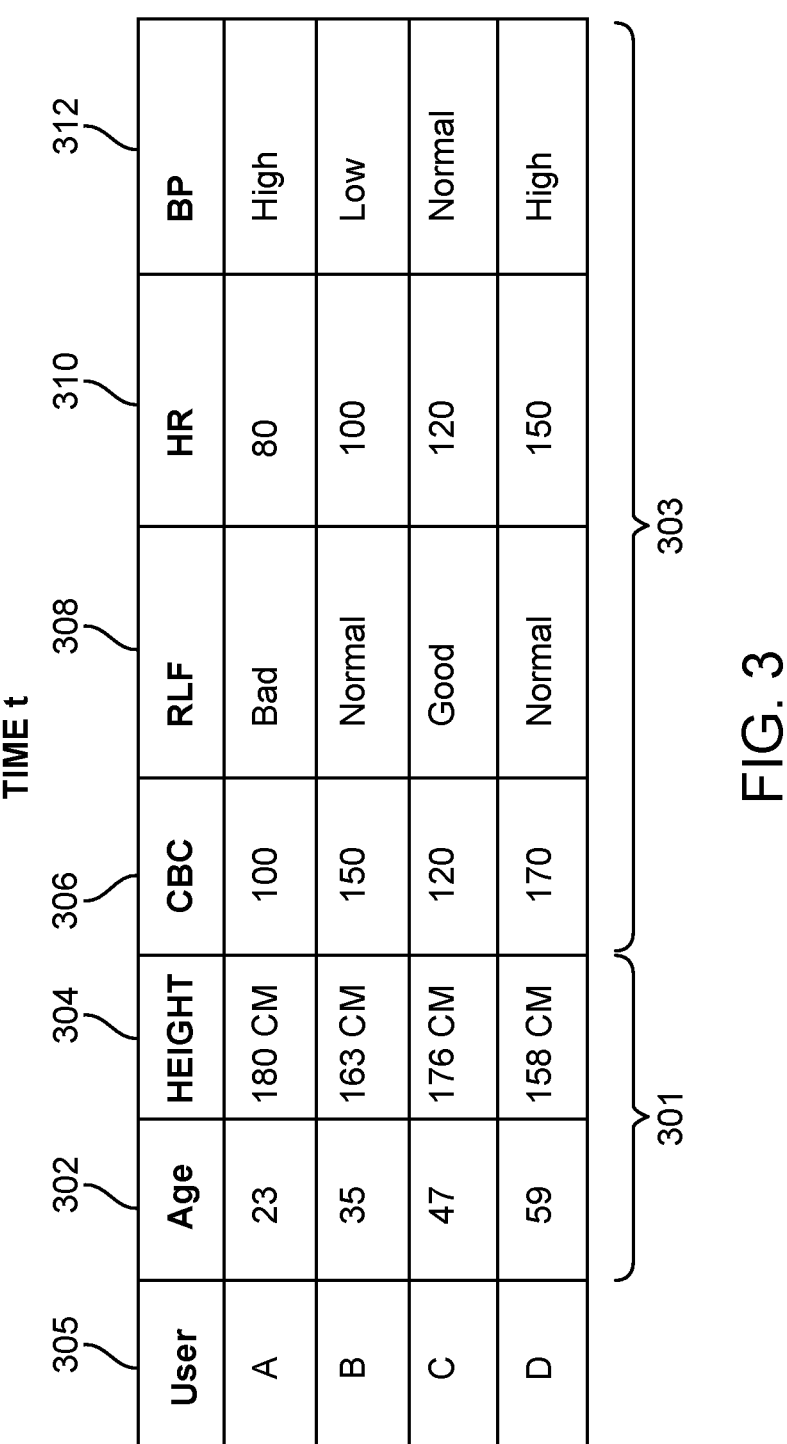
Figure 4:
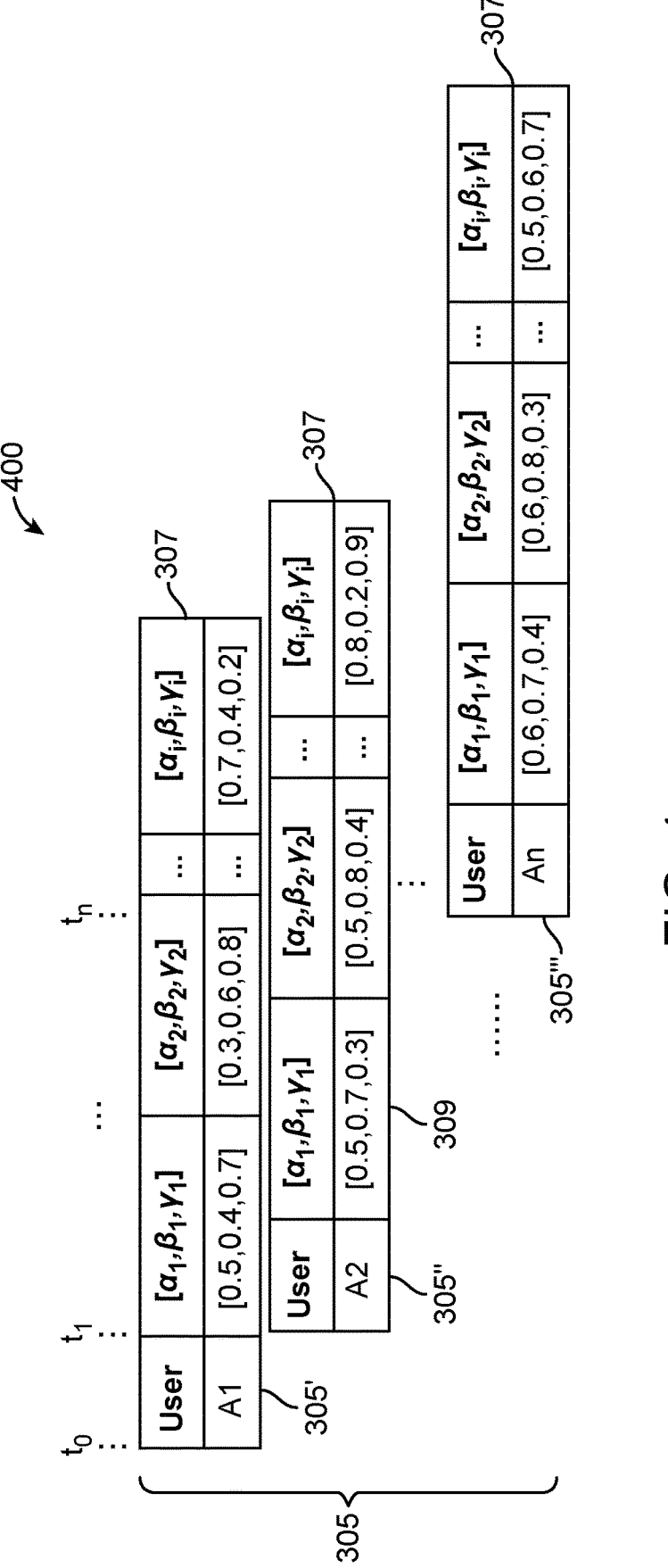
Figure 5:
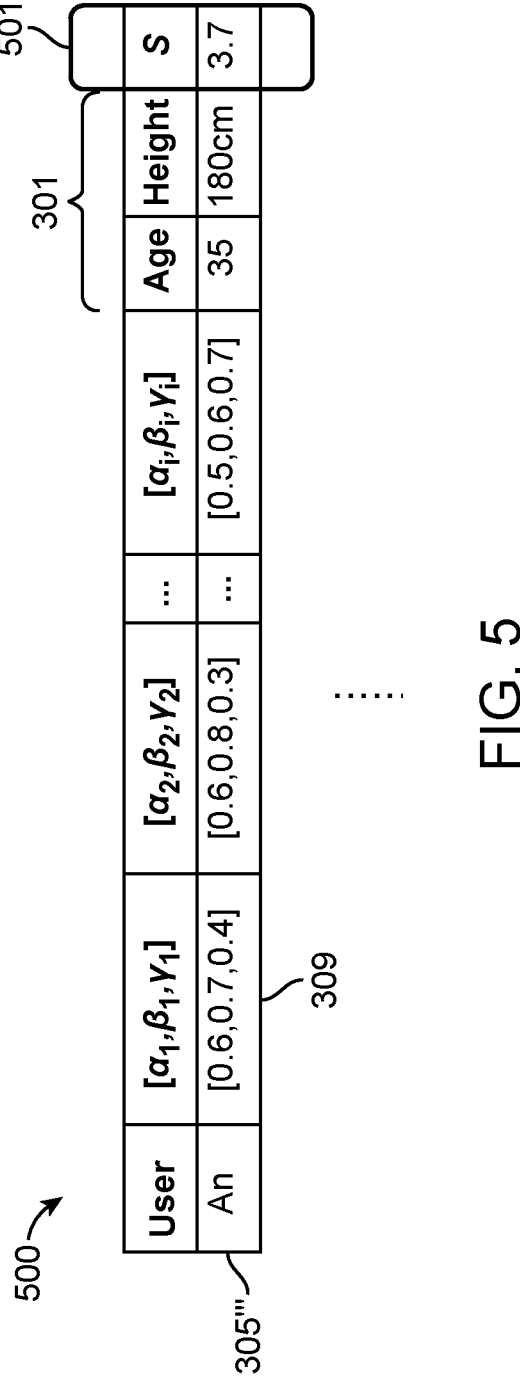

FIG. 3 depicts an example data set for target and reference objects in the process of FIG. 1;

FIG. 4. depicts a single object's data split into multiple profiles in the process of FIG. 1;

FIG. 5 depicts a similarity score for a reference profile; and

Figure 6:
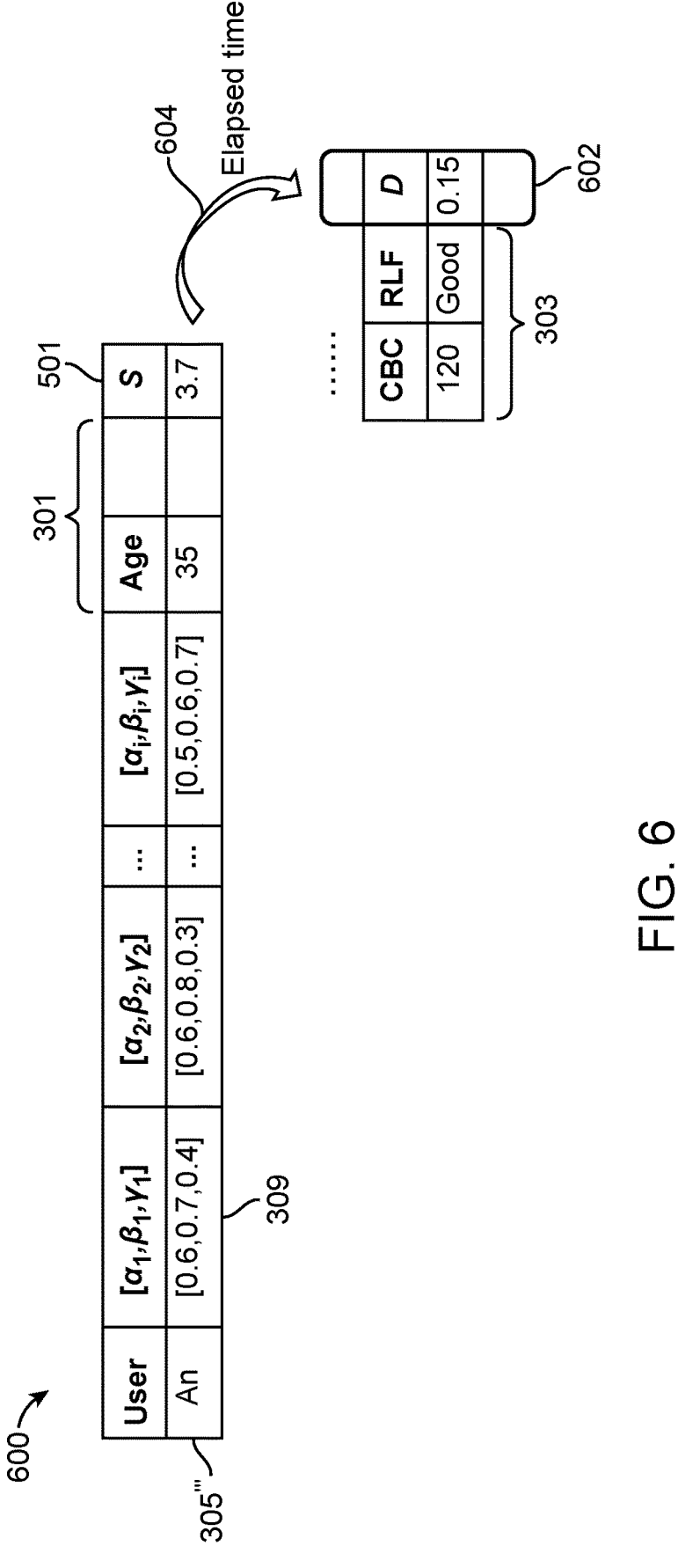

FIG. 6 depicts a difference between a target goal and a most similar reference profile.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two- or three-digit reference numbers. With minor exceptions, the leftmost digit(s) of each reference number correspond to the figure in which its element is first illustrated.

DETAILED DESCRIPTION

In one embodiment, a computer-implemented method includes receiving a set of static characteristics of a target object and a set of dynamic characteristics of the target object, and a health objective of the target object. The set of dynamic characteristics vary over time. A set of reference object data including a plurality of reference objects of the same object type as the target object is retrieved. The reference object data has a set of static characteristics for each reference object in the plurality of reference objects and a set of dynamic characteristics for each reference object in the plurality of reference objects. The set of dynamic characteristics for each reference object varies over time. The set of dynamic characteristics of the target object and the set of dynamic characteristics for each reference object in the plurality of reference objects are parameterized using a time series model. Each set of dynamic characteristics for each reference object is split into a plurality of reference profiles using the parameterized dynamic characteristics. A set of similar reference profiles is identified. The set of similar reference profiles is a subset of the plurality of reference profiles with each reference profile in the set of similar reference profiles having a higher similarity metric than each reference profile excluded from the set of similar reference profiles. A goal difference between the health objective of the target object and an end state of each reference profile in the set of similar reference profiles is determined. The reference profile in the set of similar reference profiles having the smallest goal difference is identified and health regimen of the reference object corresponding to the reference profile having the smallest goal difference in the target object is implemented. The method advantageously identifies a closest reference object and causes implementation of the most health regimen most likely to provide the desired health result of the target object.

In some examples of the method, the target object is an individual person thereby allowing for a health regimen specific to the individual to be determined.

In yet further examples of the method, the health objective is one of a fitness goal and a medical result thereby allowing for specific fitness programs or medical programs best suited to achieve the desired health goal to be implemented.

In yet further examples of the method, implementing the health regimen of the reference object corresponding to the reference profile having the smallest goal difference in the target object includes one of providing a fitness regimen to the target object and implementing a medical care regimen on the target object thereby ensuring that the health regimen is enacted.

In yet further examples of the method, the target object is a computer system, the health objective is a computer system lifecycle, and implementing the health regimen of the reference object corresponding to the reference profile having the smallest goal difference in the target object includes implementing a maintenance and update schedule of the reference object corresponding to the reference profile having the smallest goal difference in the target object. In this embodiment allows for improved maintenance scheduling and longer uptime for computer systems.

In yet further examples of the method, parameterizing the set of dynamic characteristics of the target object and the set of dynamic characteristics for each reference object in the plurality of reference objects using a time series model includes applying a Holt-Winter exponential smoothing model including three parameters to the set of dynamic characteristics of the target object and the set of dynamic characteristics for each reference object in the plurality of reference objects.

In yet further examples of the method, within the plurality of reference profiles each reference profile represents a current health status of the corresponding reference object at a given time step and includes time series information of the corresponding reference object proceeding onwards from the given time step, thereby allowing for a substantially increased number of potential reference profiles.

In yet further examples, of the method the number of reference profiles is equal to a number of time steps in the set of dynamic characteristics for each reference object in the plurality of reference objects, thereby maximizing the number of potential reference profiles.

In another aspect of the invention, a system includes a processor and a memory with the memory storing instructions for causing the processor to perform the following method: Receiving a set of static characteristics of a target object and a set of dynamic characteristics of the target object, and a health objective of the target object. The set of dynamic characteristics varies over time. A set of reference object data including a plurality of reference objects of the same object type as the target object is retrieved. The reference object data has a set of static characteristics for each reference object in the plurality of reference objects and a set of dynamic characteristics for each reference object in the plurality of reference objects. The set of dynamic characteristics for each reference object varies over time. The set of dynamic characteristics of the target object and the set of dynamic characteristics for each reference object in the plurality of reference objects are parameterized using a time series model. Each set of dynamic characteristics for each reference object is split into a plurality of reference profiles using the parameterized dynamic characteristics. A set of similar reference profiles is identified. The set of similar reference profiles is a subset of the plurality of reference profiles with each reference profile in the set of similar reference profiles having a higher similarity metric than each reference profile excluded from the set of similar reference profiles. A goal difference between the health objective of the target object and an end state of each reference profile in the set of similar reference profiles is determined. The reference profile in the set of similar reference profiles having the smallest goal difference is identified and health regimen of the reference object corresponding to the reference profile having the smallest goal difference in the target object is implemented. The computer system provides a system for implementing the method which advantageously identifies a closest reference object and causes implementation of the most health regimen most likely to provide the desired health result of the target object.

In some examples of the system, the target object is an individual person thereby allowing for a health regimen specific to the individual to be determined.

In yet further examples of the system, the health objective is one of a fitness goal and a medical result thereby allowing for specific fitness programs or medical programs best suited to achieve the desired health goal to be implemented.

In yet further examples of the system, implementing the health regimen of the reference object corresponding to the reference profile having the smallest goal difference in the target object includes one of providing a fitness regimen to the target object and implementing a medical care regimen on the target object thereby ensuring that the health regimen is enacted.

In yet further examples of the system, the target object is a computer system, the health objective is a computer system lifecycle, and implementing the health regimen of the reference object corresponding to the reference profile having the smallest goal difference in the target object includes implementing a maintenance and update schedule of the reference object corresponding to the reference profile having the smallest goal difference in the target object. In this embodiment allows for improved maintenance scheduling and longer uptime for computer systems.

In yet further examples of the system, parameterizing the set of dynamic characteristics of the target object and the set of dynamic characteristics for each reference object in the plurality of reference objects using a time series model includes applying a Holt-Winter exponential smoothing model including three parameters to the set of dynamic characteristics of the target object and the set of dynamic characteristics for each reference object in the plurality of reference objects.

In yet further examples of the system, within the plurality of reference profiles each reference profile represents a current health status of the corresponding reference object at a given time step and includes time series information of the corresponding reference object proceeding onwards from the given time step, thereby allowing for a substantially increased number of potential reference profiles.

In yet further examples, of the system the number of reference profiles is equal to a number of time steps in the set of dynamic characteristics for each reference object in the plurality of reference objects, thereby maximizing the number of potential reference profiles.

Yet another aspect of the inventions contained herein includes a computer program product having a non-transitory memory. The memory stores instructions configured to cause a computer system to perform a method including the steps of: Receiving a set of static characteristics of a target object and a set of dynamic characteristics of the target object, and a health objective of the target object. The set of dynamic characteristics varies over time. A set of reference object data including a plurality of reference objects of the same object type as the target object is retrieved. The reference object data has a set of static characteristics for each reference object in the plurality of reference objects and a set of dynamic characteristics for each reference object in the plurality of reference objects. The set of dynamic characteristics for each reference object varies over time. The set of dynamic characteristics of the target object and the set of dynamic characteristics for each reference object in the plurality of reference objects are parameterized using a time series model. Each set of dynamic characteristics for each reference object is split into a plurality of reference profiles using the parameterized dynamic characteristics. A set of similar reference profiles is identified. The set of similar reference profiles is a subset of the plurality of reference profiles with each reference profile in the set of similar reference profiles having a higher similarity metric than each reference profile excluded from the set of similar reference profiles. A goal difference between the health objective of the target object and an end state of each reference profile in the set of similar reference profiles is determined. The reference profile in the set of similar reference profiles having the smallest goal difference is identified and health regimen of the reference object corresponding to the reference profile having the smallest goal difference in the target object is implemented. The computer program product provides a physical means for distributing and, installing on computer systems, the method which advantageously identifies a closest reference object and causes implementation of the most health regimen most likely to provide the desired health result of the target object.

In some examples of the computer program product, the target object is an individual person thereby allowing for a health regimen specific to the individual to be determined.

In yet further examples of the computer program product, the health objective is one of a fitness goal and a medical result thereby allowing for specific fitness programs or medical programs best suited to achieve the desired health goal to be implemented.

In yet further examples of the computer program product, implementing the health regimen of the reference object corresponding to the reference profile having the smallest goal difference in the target object includes one of providing a fitness regimen to the target object and implementing a medical care regimen on the target object thereby ensuring that the health regimen is enacted.

In yet further examples of the computer program product, the target object is a computer system, the health objective is a computer system lifecycle, and implementing the health regimen of the reference object corresponding to the reference profile having the smallest goal difference in the target object includes implementing a maintenance and update schedule of the reference object corresponding to the reference profile having the smallest goal difference in the target object. In this embodiment allows for improved maintenance scheduling and longer uptime for computer systems.

In yet further examples of the computer program product, parameterizing the set of dynamic characteristics of the target object and the set of dynamic characteristics for each reference object in the plurality of reference objects using a time series model includes applying a Holt-Winter exponential smoothing model including three parameters to the set of dynamic characteristics of the target object and the set of dynamic characteristics for each reference object in the plurality of reference objects.

In yet further examples of the computer program product, within the plurality of reference profiles each reference profile represents a current health status of the corresponding reference object at a given time step, and includes time series information of the corresponding reference object proceeding onwards from the given time step, thereby allowing for a substantially increased number of potential reference profiles.

In yet further examples, of the computer program product the number of reference profiles is equal to a number of time steps in the set of dynamic characteristics for each reference object in the plurality of reference objects, thereby maximizing the number of potential reference profiles.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

Each of the further implementations and additional examples can be included alone or in any combination with any number of further implementations and additional examples and still fall within the aspects of the invention disclosed herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e., one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Referring now to FIG. 1, computing environment 100 includes an example of an environment for the execution of at least some of the computer code involved in performing the inventive methods, such as determining a regimen to improve a health parameter of an object module 200 (also referred to herein as block 200). In addition to block 200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 200, as identified above), peripheral device set 114 (including user interface (UI), device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 200 in persistent storage 113.

COMMUNICATION FABRIC 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface type operating systems that employ a kernel. The code included in block 200 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made though local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

It is to be understood that the block diagram of FIG. 1 is not intended to indicate that the computing environment 100 is to include all of the components shown in FIG. 1. Rather, the computing environment 100 can include any appropriate fewer or additional components not illustrated in FIG. 1 (e.g., additional memory components, embedded controllers, modules, additional network interfaces, etc.). Further, the embodiments described herein with respect to the computing environment 100 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Turning now to an overview of technologies that are more specifically relevant to aspects of the invention, when analyzing a health of an object existing systems and processes typically look to one or more parameters that are indicative of an overall health. As a result, individuals can frequently place excess emphasis on the specific parameter values, and on activities that are believed to improve those values, rather than on actions that improve the overall health of the object. This focus can lead to increasing types and amounts of actions focused on the specific parameter(s) which can, in turn, lead to more harm than good when the amount and/or type of the activities are not sufficiently varied or occur too often.

Turning now to an overview of the aspects of the invention, one or more embodiments of the invention address the above-described shortcomings of the prior art by providing a time series parameterization of both a target object and reference objects and determining a goal difference between a goal state of the target object and the end states of the reference objects. The goal difference, and the time series parameterization is used to determine a best similarity case between the goal states of the target object and one of the time series parameterized reference objects. A regimen for improving and/or maintaining the health of the target object is determined based on the activities of the best similarity reference object. In some examples, individual reference objects can be split into multiple time series parameterized profiles and each time series parameterized profile provides an independently usable reference object.

The above-described aspects of the invention address the shortcomings of the prior art by identifying similar starting points with similar goals and desirable results, thereby allowing a regimen to be selected that improves overall health without implementing activities or activity patterns that inadvertently negatively impact the overall health of the object.

Figure 2:
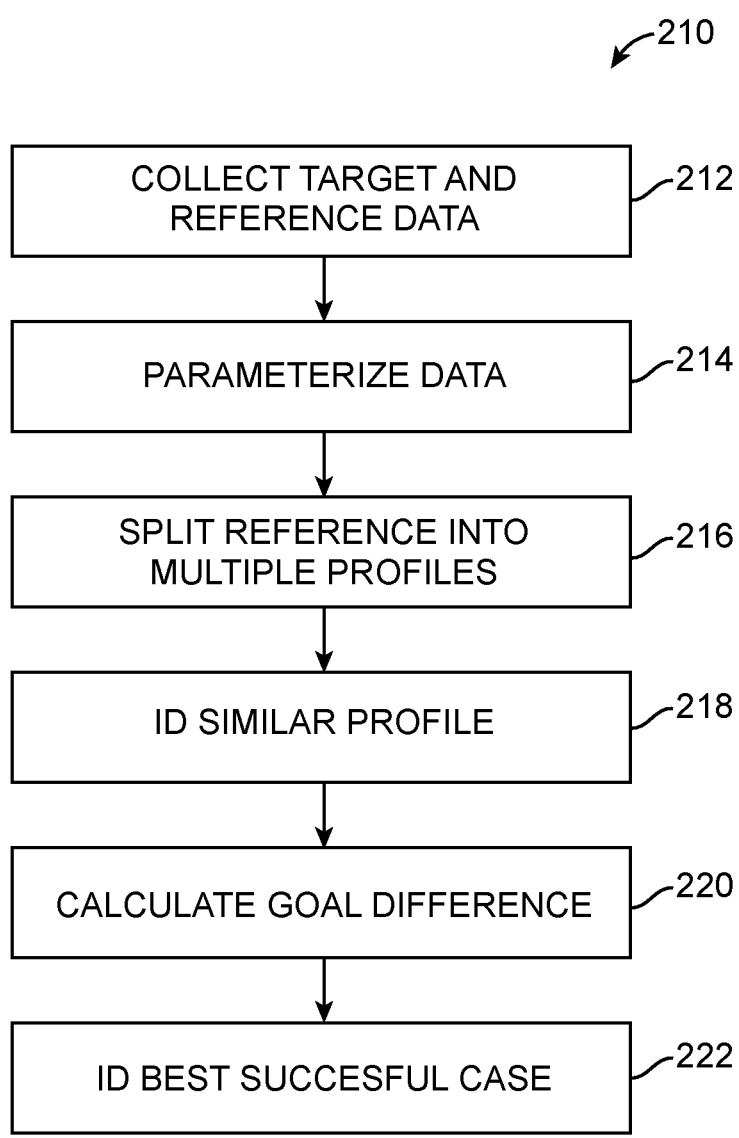
FIG. 2 depicts a flow chart of a method for identifying a best course of action to achieve a healthy object according to one embodiment.

Turning now to a more detailed description of aspects of the present invention, FIG. 2 depicts a general process 210 according to embodiments of the invention. FIGS. 3-6 illustrate particular examples of corresponding steps of the general process 210. Initially, a target object with a desired health goal is identified and reference objects of a same type having established sets of data over time are gathered in a "Collect Target and Reference Data" step 212. In one example, the target object is an individual person with a particular health goal. In another example, the target object is a server within a cloud computing environment. In each example, the reference objects are similar objects (e.g. other individual people or the same server within a cloud computing environment but in different time periods or other servers within similar cloud computing environments) and the similar objects have data sets of established health parameters over time and corresponding activity regimens. The data sets can be identified within established data systems including anonymized patient data in a health care system, established computer systems data, or any other relevant source of times series data.

FIG. 3 illustrates one specific example of the collected reference data at a given time point t. for each reference object, specific static characteristics (static data 301) of the object are collected. The static characteristics of the object include any characteristics that do not change over time, or that uniformly change over time, across the entire population of reference objects. When the reference objects (and the target object) are adult individuals such as in the example illustrated in FIG. 3, the static characteristics include demographic information such as age 302 and height 304. In alternative examples, the static characteristics can include any number of additional characteristics that either remain approximately constant (within expected bounds of variation) or change at a predictable rate (e.g., age).

In addition to the static data 301, each reference object (users 305) has a set of dynamic characteristics 303 including complete blood cell count (CBC) 306, renal and liver function (RLF) 308, heart rate (HR) 310, and blood pressure (BP) 312. Alternative or additional dynamic data can include any data about the object that changes over time. In a typical implementation, the most relevant dynamic data 303 will be data that is directly related to, or representative of, the goal. By way of example, when the objective is an improvement in athletic capability of an individual, the HR 310 and CBC 306 provide information of particular relevance. Additional information that can be tracked, such as resting heart rate, steps per day, sleep quality, heart rate variability, oxygen saturation, etc. can likewise be included within the reference data. The dynamic characteristics 303 are updated at each time t.

In at least one alternate example, the health of a cloud systems server, or other computer component, can be the target and current or past servers in a similar computing environment reference objects. In such an example, the static characteristics 301 can include a memory capacity, a storage capacity, a number of cores and/or threads of the computer server, and the dynamic characteristics 303 can include CPU usage as a percentage of CPU utilization over time, memory usage as an amount of RAM in use over time, network traffic as incoming and outgoing data transfer rates over time, disk input/output (I/O) as read and write speeds on storage devices over time, and system load as average system load over time and/or the number of jobs running over time. The listed static characteristics 301 and dynamic characteristics 303 are exemplary only and can include less than all the exemplary characteristics 301, 303 and/or additional characteristics 301/303.

Once the target and the reference data have been collected, the identified reference data is parameterized with time series model coefficients to generate a time series model of the reference data in a "Parameterize Data" step 214. In this step 214, for each dynamic characteristic, the process 210 performs a series model over time and builds a time series model. By way of example, a Holt-Winter exponential smoothing model including three parameters may be used to build the time-series model. In alternate examples, alternative time series models may be used to similar effect. The model coefficients are used to define the dynamic characteristics according to $ES(\alpha,\beta,\gamma)$, where $\alpha$ represents Level, $\beta$ represents Trend, $\gamma$ represents Seasonal in an ES model. In this way, each reference object is represented with a combined ES model coefficients: $f_n$ $(\alpha_1,\beta_1,\gamma_1, \ldots \alpha_n,\beta_n,\gamma_n)$, where n represents the number of observed physical characteristics.

In examples where the target object has data over time (e.g., an individual person has established health data or an individual server has established operational parameters) the data for the target object can likewise be parameterized using the time series model coefficients in the step 214, and provide an over time matching to reference objects, rather than being limited to a static starting data set.

Each of the reference objects is then split into multiple profiles with specific time frames in a "Split Reference(s) Into Multiple Profiles" step 216. Each profile represents a current health status of the object at a given time step, and includes time series information of the object proceeding onwards from that time step. Each profile is described using the same time series model coefficients, and can be independently compared to the target object, thereby establishing a substantially larger number of reference object profiles than actual reference objects.

One example implementation 400 of step 216, applying the data sets 301, 303 from FIG. 3, is illustrated in FIG. 4 at times $t_0$ (starting), $t_1$ (one time step subsequent to starting, and $t_k$ (n time steps subsequent to starting). When the target and reference objects are adult individuals, the time steps can be the frequency at which relevant data is updated. By way of example, if data such as HR 310 is updated each evening, the time steps can be 24 hour days. In contrast, when the target and reference objects are computer systems, such as cloud servers, the data can be updated much more frequently and time steps as low as seconds or minutes can be utilized.

Each reference object 305 is split into multiple objects 305', 305", 305''', with each object 305', 305", 305''' corresponding to the base reference object 305 starting the time series parameterization from a given time step t. Each object 305', 305", 305''' is then stored as a distinct reference profile 307. In this way, each reference profile 307 provides a distinct starting data set corresponding to the static and dynamic data from the time step t at the start of the specific profile 407, and using the time series data generate by all time steps t subsequent to the starting point. Each profile includes multiple time series steps 309, with each time series step 309 including a corresponding set of ES model coefficients.

After establishing the multiple profiles, all profiles across all established reference data are compared to the target object to identify a similar profile in an "ID Similar Profile" step 218. Similar profiles are reference data object profiles with starting parameters within threshold ranges of the target object's starting parameters, and an ending point within a range of the target objects goals. The magnitude of the thresholds for the threshold ranges depend on the particular parameter and can be set by one of skill in the art. FIG. 5 illustrates one example similarity profile 500 for a given profile. In the example of FIG. 5, the closest user profile 500 is identified by appending the static data set 301 to the ES model coefficients of each reference profile 305', 305", 305''' and using an established algorithm, such as a K-Nearest Neighbor (KNN) algorithm, to calculate a similarity value S 501. In alternative examples, alternative similarity algorithms may be used to calculate the similarity value S 501 between the target object and each reference object 305. The reference object that has the highest similarity value S 501 is identified as the closest reference object 305 and will be the reference object 305 with the most similar status among the profiles of the reference objects 305. During step 218 a set number of reference profiles with similarity values S 501 above a threshold similarity are identified and stores in a similar profiles set.

A difference between the goal health of the target object, and the end health of each similar profile is calculated in a "Calculate Goal Difference" step 220. The Goal differences are calculated by initially setting a goal for the target object and identifying metrics reflective of the goal. In the case of an adult individual this can include the metrics corresponding to a health-related outcome. By way of example, the "goal" may be to have a healthy fitness level, and the corresponding metrics may be the HR 310 and BP 312. The process 210 then compares each profile in the similar profiles set, to the target object, and calculates a goal difference 602 between the results of the reference object(s) after an elapsed time 604 and the goal of the target object. This value is quantified with a numerical representation. The goal difference is a normalized difference between the "goal" of target object and the corresponding value of the reference object profile(s) at the end of an elapsed time. By way of example, the "goal" of target object is set as improving the HR as a target value $HR_{target}$, and the HR of a reference object profile at the end of an elapsed time is $HR_{reference}$. The goal difference is calculated by:

$$\text{Goal Difference} = abs(HR_{reference} - HR_{target})/\text{Range}_{HR}$$

where abs( ) is the absolute value function to ensure the difference is always positive, and $\text{Range}_{HR}$ is the possible range of HR, the range can be calculated using (maximum value of HR-minimum value of HR) in the ordinary course.

The goal differences within the similar profiles set are compared to identify the reference profile with the smallest goal difference in an "ID Best Successful Case" step 222. The reference profile with the smallest goal difference represents the profile with the closest outcome to the target outcome. Once the best successful case has been selected, the regimen of the selected profile that was followed to result in the outcome is identified and followed by the target object to achieve the desired goal without engaging in potentially harmful excess activities and/or extraneous or unhelpful activities.

Use of the process 210 expresses the characteristics of the user objects through coefficients derived from multiple time series models and dynamically represents the states of a single reference object through multiple time intervals thereby capturing the varying states of the reference object at different time stages. This allows the process 210 to predict and assess a developmental trajectory of the target object by leveraging historical states of the other similar or related objects (the reference objects).

The process 210 can be applied, in one example, as a recommendation tool in sports and/or personal health applications to recommend appropriate sports and/or exercise regimens.

The process 210 can be applied, in another example, as a computer aided diagnostic tool in medical institutions to assist in identifying successful care routines for sick or injured individuals.

The process 210 can be applied, in yet another example, as a server monitoring tool for cloud computing servers to assist in scheduling maintenance, balancing loads, and optimizing server operations to increase the server lifecycle.

The process 210 can be applied, in yet another example, as a maintenance tool to identify and implement a maintenance schedule for one or more machines or lines in a manufacturing plant based on the frequency of operations of the plant.

The above example implementations are non-limiting, and the process 210 can be applied in any number of similar situations and systems without being limited to the specifically enumerated example applications.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
receiving a set of static characteristics of a target object, a set of dynamic characteristics of the target object at a processor, and a health objective of the target object, wherein the set of dynamic characteristics vary over time, wherein the target object is a computer system, wherein the health objective is a computer system lifecycle, wherein the static characteristics include a memory capacity, a storage capacity, and one of a number of cores and a a number of threads of the computer system, and wherein the set of dynamic characteristics include central processing unit (CPU) usage as a percentage of CPU utilization over time, memory usage as an amount of RAM in use over time, network traffic as incoming and outgoing data transfer rates over time, disk input/output (I/O) as read and write speeds on storage devices over time, and system load as average system load over time and/or the number of jobs running over time; and
defining a goal of the target object and identifying quantifiable metrics reflective of the goal;
retrieving a set of reference object data, the reference object data including a plurality of reference objects of the same object type as the target object, the reference object data having a set of static characteristics for each reference object in the plurality of reference objects and a set of dynamic characteristics for each reference object in the plurality of reference objects, the set of dynamic characteristics for each reference object varying over time;
parameterizing the set of dynamic characteristics of the target object and the set of dynamic characteristics for each reference object in the plurality of reference objects using a time series model;
splitting each set of dynamic characteristics for each reference object into a plurality of reference profiles using the parameterized dynamic characteristics, wherein each reference profile in the plurality of reference profiles includes a current health status of the reference object at a time step and time series information of the reference object proceeding onwards from the time step;
identifying a set of similar reference profiles, the set of similar reference profiles being a subset of the plurality of reference profiles with each reference profile in the set of similar reference profiles having a higher similarity metric than each reference profile excluded from the set of similar reference profiles;
determining a goal difference between the goal of the target object and an end state of each reference profile in the set of similar reference profiles, wherein determining the goal difference includes determining a difference between the quantifiable metrics of the goal and corresponding quantifiable metrics of each reference profile in the set of similar reference profiles; and
identifying the reference profile in the set of similar reference profiles having the smallest goal difference and implementing a health regimen of the reference object corresponding to the reference profile having the smallest goal difference in the target object, wherein implementing the health regimen of the reference object corresponding to the reference profile having the smallest goal difference in the target object includes implementing a maintenance and update schedule of the reference object corresponding to the reference profile having the smallest goal difference in the target object.

2. The computer-implemented method of claim 1, wherein parameterizing the set of dynamic characteristics of the target object and the set of dynamic characteristics for each reference object in the plurality of reference objects using a time series model comprises applying a Holt-Winter exponential smoothing model including three parameters to the set of dynamic characteristics of the target object and the set of dynamic characteristics for each reference object in the plurality of reference objects.

3. The computer-implemented method of claim 1, wherein within the plurality of reference profiles each reference profile represents a current health status of the corresponding reference object at a given time step, and includes time series information of the corresponding reference object proceeding onwards from the given time step.

4. The computer-implemented method of claim 3, wherein a number of reference profiles is equal to a number of time steps in the set of dynamic characteristics for each reference object in the plurality of reference objects.

5. A system comprising:
a processor and a memory, wherein the memory stores instructions for causing the processor to perform the steps of:
receiving a set of static characteristics of a target object, a set of dynamic characteristics of the target object at a processor, and a health objective of the target object, wherein the set of dynamic characteristics vary over time, wherein the target object is a computer system, wherein the health objective is a computer system lifecycle, wherein the static characteristics include a memory capacity, a storage capacity, and one of a number of cores and a number of threads of the computer system, and wherein the set of dynamic characteristics include central processing unit (CPU) usage as a percentage of CPU utilization over time, memory usage as an amount of RAM in use over time, network traffic as incoming and outgoing data transfer rates over time, disk input/output (I/O) as read and write speeds on storage devices over time, and system load as average system load over time and/or the number of jobs running over time; and;

retrieving a set of reference object data, the reference object data including a plurality of reference objects of the same object type as the target object, the reference object data having a set of static characteristics for each reference object in the plurality of reference objects and a set of dynamic characteristics for each reference object in the plurality of reference objects, the set of dynamic characteristics for each reference object varying over time;

parameterizing the set of dynamic characteristics of the target object and the set of dynamic characteristics for each reference object in the plurality of reference objects using a time series model;

splitting each set of dynamic characteristics for each reference object in the plurality of reference profiles into a plurality of new reference profiles using the parameterized dynamic characteristics, and creating a new set of reference profiles including each reference profile in the plurality of new reference profiles, wherein each reference profile in the plurality of new reference profiles includes a current health status of the reference object at a time step and time series information of the reference object proceeding onwards from the time step;

identifying a set of similar reference profiles, the set of similar reference profiles being a subset of the plurality of reference profiles with each reference profile in the set of similar reference profiles having a higher similarity metric than each reference profile excluded from the set of similar reference profiles;

determining a goal difference between the health objective of the target object and an end state of each reference profile in the set of similar reference profiles; and identifying the reference profile in the set of similar reference profiles having the smallest goal difference and implementing a health regimen of the reference object corresponding to the reference profile having the smallest goal difference in the target object, wherein implementing the health regimen of the reference object corresponding to the reference profile having the smallest goal difference in the target object includes implementing a maintenance and update schedule of the reference object corresponding to the reference profile having the smallest goal difference in the target object.

6. The system of claim 5, wherein parameterizing the set of dynamic characteristics of the target object and the set of dynamic characteristics for each reference object in the plurality of reference objects using a time series model comprises applying a Holt-Wagner exponential smoothing model including three parameters to the set of dynamic characteristics of the target object and the set of dynamic characteristics for each reference object in the plurality of reference objects.

7. The system of claim 5, wherein within the plurality of reference profiles each reference profile represents a current health status of the corresponding reference object at a given time step, and includes time series information of the corresponding reference object proceeding onwards from the given time step.

8. The system of claim 7, wherein a number of reference profiles is equal to a number of time steps in the set of dynamic characteristics for each reference object in the plurality of reference objects.

9. A computer program product comprising a non-transitory memory storing instructions configured to cause a computer system to perform a method including the steps of:

receiving a set of static characteristics of a target object, a set of dynamic characteristics of the target object at a processor, and a health objective of the target object, wherein the set of dynamic characteristics vary over time;

retrieving a set of reference object data, the reference object data including a plurality of reference objects of the same object type as the target object, the reference object data having a set of static characteristics for each reference object in the plurality of reference objects and a set of dynamic characteristics for each reference object in the plurality of reference objects, the set of dynamic characteristics for each reference object varying over time, wherein the target object is a computer system, wherein the health objective is a computer system lifecycle, wherein the static characteristics include a memory capacity, a storage capacity, and one of a number of cores and a number of threads of the computer system, and wherein the set of dynamic characteristics include central processing unit (CPU) usage as a percentage of CPU utilization over time, memory usage as an amount of RAM in use over time, network traffic as incoming and outgoing data transfer rates over time, disk input/output (I/O) as read and write speeds on storage devices over time, and system load as average system load over time and/or the number of jobs running over time; and;

parameterizing the set of dynamic characteristics of the target object and the set of dynamic characteristics for each reference object in the plurality of reference objects using a time series model;

splitting each set of dynamic characteristics for each reference object in the plurality of reference profiles into a plurality of new reference profiles using the parameterized dynamic characteristics and creating a new set of reference profiles including each reference profile in the plurality of new reference profiles, wherein each reference profile in the plurality of new reference profiles includes a current health status of the reference object at a time step and time series information of the reference object proceeding onwards from the time step;

identifying a set of similar reference profiles, the set of similar reference profiles being a subset of the plurality of new reference profiles with each reference profile in the set of similar reference profiles having a higher similarity metric than each reference profile excluded from the set of similar reference profiles;

determining a goal difference between the health objective of the target object and an end state of each reference profile in the set of similar reference profiles; and identifying the reference profile in the set of similar reference profiles having the smallest goal difference and implementing a health regimen of the reference object corresponding to the reference profile having the smallest goal difference in the target object, wherein implementing the health regimen of the reference object corresponding to the reference profile having the smallest goal difference in the target object includes implementing a maintenance and update schedule of the reference object corresponding to the reference profile having the smallest goal difference in the target object.

10. The computer program product of claim 9, wherein parameterizing the set of dynamic characteristics of the target object and the set of dynamic characteristics for each reference object in the plurality of reference objects using a time series model comprises applying a Holt-Winter exponential smoothing model including three parameters to the set of dynamic characteristics of the target object and the set of dynamic characteristics for each reference object in the plurality of reference objects.

11. The computer program product of claim 9, wherein within the plurality of reference profiles each reference profile represents a current health status of the corresponding reference object at a given time step, and includes time series information of the corresponding reference object proceeding onwards from the given time step.

12. The computer program product of claim 10, wherein a number of reference profiles is equal to a number of time steps in the set of dynamic characteristics for each reference object in the plurality of reference objects.

* * * * *